United States Patent [19]

DeLuca et al.

[11] Patent Number: 5,563,286
[45] Date of Patent: Oct. 8, 1996

[54] SYNTHESIS OF 19-NOR VITAMIN D COMPOUNDS

[75] Inventors: Hector F. DeLuca, Deerfield; Heinrich K. Schnoes; Kato L. Perlman, both of Madison, all of Wis.; Rolf E. Swenson, Lake Bluff, Ill.

[73] Assignee: Wisconsin Alumni Research Foundation, Madison, Wis.

[21] Appl. No.: 441,878

[22] Filed: May 16, 1995

Related U.S. Application Data

[62] Division of Ser. No. 329,334, Oct. 26, 1994, Pat. No. 5,486,636, which is a division of Ser. No. 180,702, Jan. 13, 1994, Pat. No. 5,391,755, which is a division of Ser. No. 979,482, Nov. 20, 1992, Pat. No. 5,281,731, which is a continuation of Ser. No. 705,917, May 28, 1991, abandoned.

[51] Int. Cl.$^6$ .............................. C07F 7/04; C07C 69/74
[52] U.S. Cl. ..................... 556/443; 556/449; 556/482; 560/126; 568/338; 568/343; 568/347; 568/350
[58] Field of Search ........................... 560/126; 556/443, 556/449, 482; 568/338, 343, 347, 350

[56] References Cited

U.S. PATENT DOCUMENTS

| | | | |
|---|---|---|---|
| 4,508,651 | 4/1985 | Baggiolini et al. | 260/397 |
| 4,607,118 | 8/1986 | Grubbs et al. | 560/60 |
| 4,612,308 | 9/1986 | Baggiolini et al. | 514/167 |
| 4,618,360 | 10/1986 | Brunner | 71/88 |
| 4,668,817 | 5/1987 | Sprecker et al. | 560/126 |
| 4,681,976 | 7/1987 | Sprecker et al. | 560/126 |
| 4,755,329 | 7/1988 | DeLuca et al. | 260/397 |
| 4,804,502 | 2/1989 | Baggiolini et al. | 260/397 |
| 5,086,191 | 2/1992 | DeLuca et al. | 552/653 |
| 5,391,755 | 2/1995 | DeLuca et al. | 556/443 |
| 5,486,636 | 1/1996 | DeLuca et al. | 556/443 |

FOREIGN PATENT DOCUMENTS

| | | |
|---|---|---|
| 0154185 | 9/1985 | European Pat. Off. |
| 0182298 | 5/1986 | European Pat. Off. |
| 0186102 | 7/1986 | European Pat. Off. |
| 0325279 | 7/1989 | European Pat. Off. |
| 0326875 | 8/1989 | European Pat. Off. |
| 0387077 | 9/1990 | European Pat. Off. |
| 0516411 | 12/1992 | European Pat. Off. |
| 2167756 | 6/1986 | United Kingdom. |
| WO86/07364 | 12/1986 | WIPO. |
| WO87/00834 | 2/1987 | WIPO. |
| WO90/09992 | 9/1990 | WIPO. |

OTHER PUBLICATIONS

Journal of The American Chemical Society, vol. 95, No. 23, Nov. 14, 1973, Gaston PA, US, pp. 7821–7828, C. D. Snyder et al, "Stereochemistry of Quinate–Shikimate Conversions. Synthesis of (−)-4-epi-Shikimic Acid".

Chemische Berichte, vol. 110, No. 1, 1977, Weinheim De, pp. 331–341, H. Paulsen et al, "Kann bei Acyloxonium–Umlagerungen ein 1,3-Prozess mit einem 1,2-Prozess Konkurrieren"?Heterocycles (Special Issue), vol. 17, 1982, pp. 209–214, M. Yoshikawa et al, "Reductive One Step Elimination of an Acetoxyl Residue at Beta Position of a Nitro Group: Syntheses of (−)-Shikimic Acid from D-Mannose and 2-Deoxystreptamine Pentaacetate from N-Acetylglucosamine".

Tetrahedron Letters, vol. 31, No. 13, 1990, Oxford GB, pp. 1823–1824, K. L. Perlman et al, "1-alpha-25-Dihydroxy-19-nor-Vitamin $D_3$, A Novel Vitamin D Related Compound with Patential Therapeutic Activity".

Tetrahedron Letters, vol. 32, No. 52, Dec. 23, 1991, Oxford GB, pp. 7663–7666, K. L. Perlman et al, "Novel Synthesis of 19-nor-Vitamin D Compounds".

Tetrahedron Letters, vol. 33, No. 21, May 19, 1992, Oxford GB, pp. 2937–2940, K. L. Perlman et al, "1-alpha-Hydroxy-19-nor-Vitamin D C22 Aldehyde. A Valuable intermediate in the Synthesis of Side Chain Modified 1-alpha, 25-Dihydroxy-19-nor-Vitamin $D_3$".

Tetrahedron: Asymmetry, vol. 3, No. 2, Feb. 1992, Oxford GB, pp. 297–306, H. Suemune et al, "Enantioselective Synthesis of (1S, 3S, 5R)-1-Acetoxy-5-Benzyl oxycyclohexan-3-ol and its Application to the Synthesis of Compactin Lactone Moiety and Quinic Acid".

Carbohydrate Research, vol. 58, No. 2, 1977, Amsterdam NL, pp. 484–487, H. Paulsen et al, "Acyloxonium–Umlagerungen von (−)-Chinaalkohol".

(List continued on next page.)

*Primary Examiner*—Kimberly J. Prior
*Attorney, Agent, or Firm*—Andrus, Sceales, Starke & Sawall

[57] ABSTRACT

A process is disclosed for the removal of the 4-protected hydroxy group from compounds of the following formula:

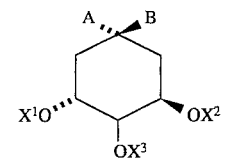

where A is —COOAlkyl and B is hydroxy, or A and B together represent either oxo or =CHCOOAlkyl, where $X^1$ and $X^2$ are the same or different and represent hydrogen or a hydroxy-protecting group, and where $X^3$ is

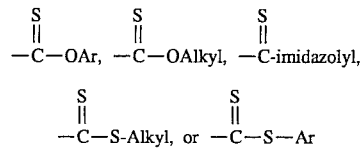

with a hydrogen radical source, such as tributyltin hydride or tris(trimethylsilyl)silane, and a radical initiator, such as AIBN or irradiation.

1 Claim, No Drawings

OTHER PUBLICATIONS

Sardina et al, Studies on the Synthesis of Side–Chain Hydroxylated Metabolites of Vitamin $D_2$. Stereocontrolled Synthesis of 25–Hydroxyvitamin $D_2$, J. Org. Chem., 51, 1264–1269, 1986.

Toh et al, Studies on a Convergent Route to Side–Chain Analogues of Vitamin D: 25–Hydroxy–23–oxavitamin $D_3$, J. Org. Chem., 48, 1414–1417, 1983.

Baggiolini et al, Stereocontrolled Total Synthesis of 1Alpha, 25–Dihydroxycholecalciferol and 1Alpha, 25–Dihydroxyergocalciferol, J. Org. Chem., 51, 3098–3108, 1986.

Lythgoe et al, Calciferol and its Relatives. Part 22. A Direct Total Synthesis of Vitamin $D_2$ and Vitamin $D_3$, J. Chem. Soc., Perkin. Trans. I, 590–595, 1978.

Lythgoe, Synthetic Approaches to Vitamin D and its Relatives, Chem. Soc. Review, 9, 449–474, 1983.

SYNTHESIS OF 19-NOR VITAMIN D COMPOUNDS

This invention was made with United States Government support awarded by the National Institutes of Health (NIH), Grant No. DK-14881. The United States Government has certain rights in this invention.

This application is a divisional of application Ser. No. 08/329,334 filed Oct. 26, 1994, now U.S. Pat. No. 5,486,636, which in turn is a divisional application of Ser. No. 08/180,702 filed Jan. 13, 1994, now U.S. Pat. No. 5,391,755 which in turn is a divisional application of Ser. No. 07/979,482 filed Nov. 20, 1992, now U.S. Pat. No. 5,281,731, which in turn is a continuation of Ser. No. 07/705,917 filed May 28, 1991, now abandoned.

BACKGROUND OF THE INVENTION

The hormone, 1α,25-dihydroxyvitamin D3, is known to be a highly potent regulator of calcium homeostasis in animals, and more recently its activity in cellular differentiation has been established, V. Ostrem, Y. Tanaka, J. Prahl, H. F. DeLuca and N. Ikekawa, *Proc. Natl. Acad. Sci. USA*, (1987), 84, 2610. Many structural analogs have been prepared and tested and some of these have been found to exhibit an interesting separation of activities in cell differentiation and calcium regulation. This difference in activity may be useful in the treatment of some cancers and osteoporosis, H. Sai, S. Takatsuto, N. Ikekawa, I. Tanaka and H. F. DeLuca, *Chem. Pharm. Bull.*, (1986), 34, 4508.

Recently, a new class of vitamin D analogs has been discovered, the so-called 19-nor-vitamin D compounds, which, as shown by the general structure below, are characterized by the replacement of the ring A-exocyclic methylene group (carbon 19), typical of the vitamin D system, by two hydrogen atoms.

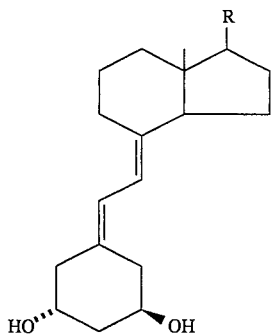

The group R in the above structure represents asteroid side chain as it occurs in any of the natural vitamin D compounds, or in synthetic analogs thereof. A specific example of a 19-nor-vitamin D compound is given by structure 20 a in Scheme IV herein. Biological testing of such 19-nor-analogs (e.g. compound 20) revealed an activity profile characterized by high potency in inducing differentiation of malignant cells, with very low calcium mobilizing activity. Thus, such compounds are potentially useful as therapeutic agents for the treatment of malignancies.

A method of synthesis of 19-nor-vitamin D compounds has been reported by Perlman et al., Tetrahedron Letters 13, 1823 (1990). However, this method, which involves the removal of the C-19-methylene group in an existing vitamin D compound is not well suited for the larger scale preparation of 19-nor analogs.

DISCLOSURE OF THE INVENTION

Described herein is a novel synthesis of 19-nor-vitamin D compounds. A characteristic element of this new method is the condensation of a ring-A unit, as represented by structure I, below, with a bicyclic-ketone of the Windaus-Grundmann type, structure II below, to obtain the desired 19-nor-vitamin D compound, structure III.

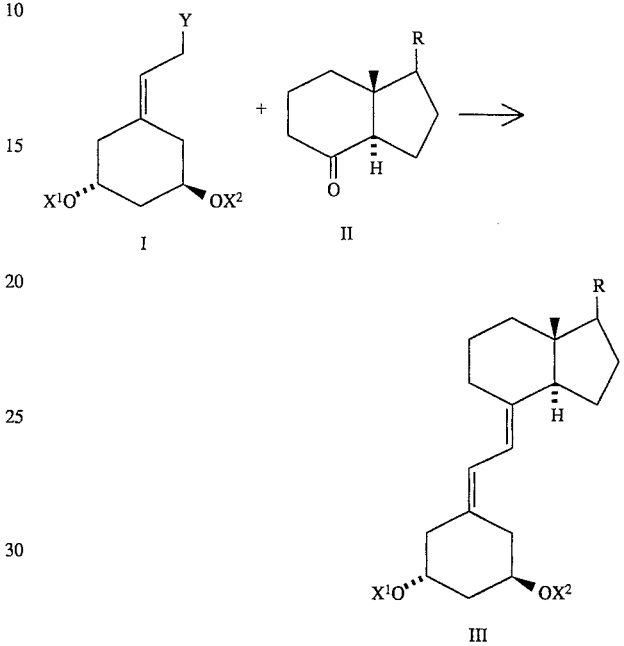

The process shown above, therefore, represents a novel application of the convergent synthesis concept, which has been applied effectively for the preparation of vitamin D compounds [e.g. Lythgoe et al., *J. Chem. Soc. Perkin Trans, I*, 590 (1978); 2386 (1976); Lythgoe, *Chem. Soc. Rev.* 9, 449 (1983); H. T. Toh and W. H. Okamura, *J. Org. Chem.* 48, 1414 (1983); E. G. Baggiolini et al., *J. Org. Chem.* 51, 3098 (1986); Sardina et al., *J. Org. Chem.* 51, 1264 (1986); *J. Org. Chem.* 51, 1269 (1986)].

Another important aspect of this invention is the preparation of ring-A units of general structure I from (−)quinic acid. In structure I, above, $X^1$ and $X^2$, which may be the same or different, represent hydroxy-protecting groups, and Y represents a grouping that renders the hydrogen on the adjacent carbon center sufficiently acidic to yield a reactive carbanion upon treatment with a strong base. Exemplary of such groupings Y are —$P(O)Ph_2$, —$P(O)(OAlkyl)_2$, —$SO_2Ar$, or —$Si(Alkyl)_3$. Compounds of type I, above, are new. Their synthesis, and other novel intermediates used in their preparation are disclosed herein.

In the bicyclic-ketone of structure II, or in the 19-nor-vitamin D compound of structure III, above, the substituent R may represent any desired group, it being understood that any functionalities in R that might be sensitive, or that interfere with the condensation reaction, be suitably protected as is well-known in the art. More specifically, R may represent, for example, hydrogen, alkyl, hydroxyalkyl, deuteralkyl, fluoroalkyl, or a side chain of the formula

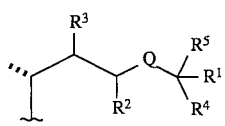

where $R^1$, $R^2$, $R^3$, independently represent hydrogen, hydroxy, protected hydroxy, or alkyl, where the bond between carbons 22 and 23 may be a single, double or triple bond, where Q is the group

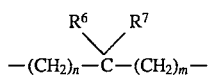

where $R^6$ and $R^7$, independently, are selected from hydrogen, alkyl, hydroxyalkyl, hydroxy, protected hydroxy, and fluoro, or where $R^6$ and $R^7$ taken together represent an oxo group or an alkylidene group, and where n and m are integers having, independently, the values 0, 1, 2, 3, 4 or 5, where $R^4$ and $R^5$, independently, represent deuteroalkyl, fluoroalkyl and the group Q—H, or $R^4$ and $R^5$, taken together, represent the group Q, with the proviso that at least one of n or m has the value of 1 or greater, and wherein the carbon at any one of positions 20, 22 or 23 in the side chain may be replaced by an O, S, or N atom.

As used in the description, and in the claims, the term "hydroxy-proteting group" refers to any group commonly used for the protection of hydroxy functions during subsequent reactions, including, for example, acyl or alkylsilyl groups such as trimethylsilyl, triethytsilyl, t-butyldimethylsilyl and analogous alkyl or arylsilyl radicals, or alkoxyalkyl groups such as methoxymethyl, ethoxymethyl, methoxyethoxymethyl, tetrahydrofuranyl or tetrahydropyranyl. A "protected-hydroxy" is a hydroxy function derivatized by one of the above hydroxy-protecting groupings. "Alkyl" represents a straight-chain or branched hydrocarbon radical of 1 to 10 carbons in all its isomeric forms, such as methyl, ethyl, propyl, isopropyl, butyl, isobutyl, pentyl, etc., and the terms "hydroxyalkyl," "fluoroalkyl" and "deuteroalkyl" refer to such an alkyl radical substituted by one or more hydroxy, fluoro or deuterium groups respectively. An "acyl" group is an alkanoyl group of 1 to 6 carbons in all its isomeric forms, or an aroyl group, such as benzoyl, or halo-, nitro- or alkyl-substituted benzoyl groups, or an alkoxycarbonyl group of the type Alkyl-O—CO—, such as methoxycarbonyl, ethoxycarbonyl, propyloxycarbonyl, etc., or a dicarboxylic acyl group such as oxalyl, malonyl, succinoyl, glutaroyl, or adiopoyl. The term "aryl" signifies a phenyl-, or an alkyl-, nitro- or halo-substituted phenyl group. The term alkoxy signifies the group alkyl-O—. Keton es of general structure II featuring homologated side chains are new compounds.

Ketones of structure II, with diverse side chain groups R, can be prepared by known methods, as documented, for example by Baggiolini et al., *J. Org. Chem.* 51, 3098 (1951); Baggiolini et al., U.S. Pat. No. 4,804,502; Sardina et al., *J. Org. Chem.* 51, 1264 (1986); Kocienski et al., *J. Chem. Soc. Perkin Trans,* 1, 834 (1978); Toh and Okamura, *J. Org. Chem.* 48, 1414 (1983); Mascovenas et al., *J. Org. Chem.,* 51, 1269 (1986). Ketones of general structure II featuring homologated side chains are new compounds.

For the preparation of ring A-synthons of structure I, a new synthetic route has been developed, based on (−)quinic acid as starting material. This substance, being commercially available and having hydroxy groups of the correct stereochemistry in desired positions is a useful synthon in vitamin D chemistry [Desmaele and Tanier, *Tetrahedron Letters,* 26, 4941 (1985)]. The overall process, in general form, is summarized by the reaction scheme below:

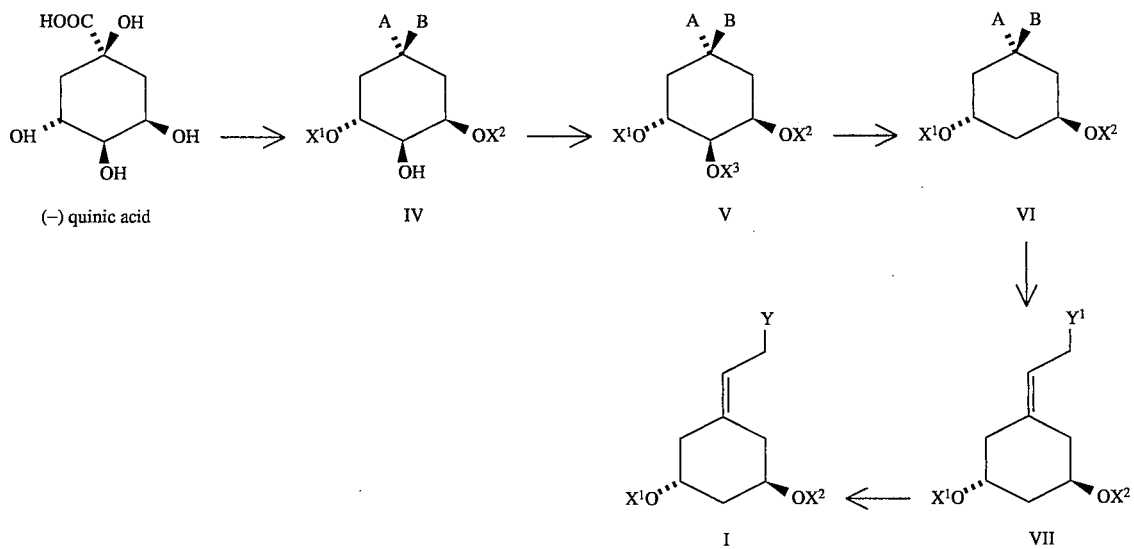

As shown in this scheme, the conversion of quinic acid to the desired ring-A unit I comprises two major synthetic transformations, namely, the removal of the central hydroxy group at carbon-4 of quinic acid, and the replacement of the carboxy and hydroxy substituents of carbon-1 by an unsaturated two-carbon side chain bearing the desired Y-functionality. It was found that the overall process can be executed in several, conceptually related variations, differing chiefly in the order in which the key synthetic operations are accomplished.

In the above structures (IV, V, VI), $X^1$ and $X^2$, which may be the same or different, represent a hydroxy-protecting group, A represents the group —COOAlkyl or —CH$_2$OH, B is hydroxy, and A and B, when taken together, represent an oxo group (=O), or =CHCOOAlkyl.

The initial steps of the overall process comprise the esterification of quinic acid, by treatment with a suitable alkyl alcohol (e.g. methanol, ethanol, propanol or higher alkanol) under acid catalysis, followed by hydroxy protection under conditions known in the art, to provide compound IV, where A is —COOAlkyl, B is hydroxy, and $X^1$ and $X^2$ are hydroxy-protecting groups. While the specific nature of $X^1$ and $X^2$ is not critical, it is understood, of course, that the protecting groups selected are both compatible with subsequent chemical transformation, and also removable when desired. Suitable are, for example, alkylsilyl- or alkylarylsilyl groups or alkoxyalkyl groups. By appropriate further transformation of the above hydroxy-protected alkyl ester, e.g. by hydride reduction of ester (thereby producing compound IV, where A is —CH$_2$OH, and B is —OH), followed by cleavage of the resulting vicinal diol, using known vicinal diol cleavage reagents, such as periodate or lead tetracetate, there is obtained the corresponding cyclohexanone derivative, i.e. compound IV, where A and B, taken together represent an oxo function and $X^1$ and $X^2$ are hydroxy-protecting groups. This ketone, in turn, after temporary protection of the remaining central hydroxy group at C-4 (e.g. acyl, alkylsilyl or alkoxyalkyl protection) can be alkylated, for example, by treatment with alkyl (trimethylsilyl) acetate in the presence of a strong base, such as NaH, lithium diisopropylamide, or an alkyl or aryl lithium base, to obtain, after removal of the temporary C-4-OH-protecting group, the alkyl cyclohexylidene ester, of general structure IV, where A and B, taken together represent the group =CHCOOAlkyl, and $X^1$ and $X^2$ are hydroxy-protecting groups.

It has been found that intermediate IV in all of the above described structural modifications can be used for the reductive removal of the C-4-hydroxy group, by means of a free radical deoxygenation procedure [Barton and McCambie, *J. Chem. Soc. Perkin Trans.* 1, 1574 (1975); Robins et al., *J. Am. Chem. Soc.* 103, 933 (1981); 105, 4059 (1983); Barton and Motherwell, *Pure & Appl. Chem.*, 53, 15 (1981)]. This process entails the conversion of the free C-4-hydroxy group in compound IV to a suitable derivative, for example, a thiono-ester or xanthate derivative, as represented by general structure V in the above reaction scheme, where $X^3$ is a grouping such as

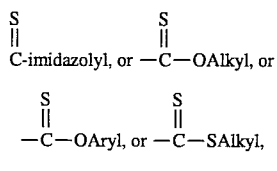

and where A, B, $X^1$ and $X^2$ have the meaning previously defined. Intermediates of type V, upon treatment with a hydrogen radical source in the presence of a radical initiator, then undergo reductive deoxygenation to furnish compounds of general structure VI, where A, B, $X^1$ and $X^2$ represent substituents as previously defined. For such deoxygenation reactions, suitable sources of hydrogen radicals are the trialkyltin hydrides (e.g. tributyltin hydride) or tris (trialkylsilyl) silanes (e.g. (Me$_3$Si)$_3$SiH) [Schummer and Hofle, *Syn. Lett.* 106 (1990); Baltestri et al., *J. Org. Chem.* 56, 678 (1991)], and suitable radical initiators are provided by azaisobutyronitrile (AIBN) or by irradiation. It is to be noted that the substituents A, B, $X^1$ and $X^2$ remain unchanged during the above described two-step deoxygenation procedure. Thus, from compound IV, where A is —COOAlkyl and B is —OH, there is obtained compound VI, where A is —COOAlkyl, and B is —OH, and likewise, compound IV, where A and B, taken together represent =O, or =CHCOOAlkyl, yields compound VI, where A and B together, represent =O, or =CHCOOAlkyl, respectively.

As in the case of the compounds of structure IV, it is possible to effect transformations of the A and B substituents of the compounds of structure VI by processes entirely analogous to those discussed in connection with the compounds of structure IV. Thus, compound VI, where A is COOAlkyl and B is hydroxy, upon ester reduction and vicinal diol cleavage, as described above for the case of compound IV, provides VI as the cyclohexanone analog, where A and B, taken together represent an oxo group, and the latter, upon alkylation as described above, yields the cyclohexylidene modification, i.e. VI, where A and B taken together represent =CHCOOAlkyl.

For the subsequent steps towards the preparation of ring A-synthon of general structure I, the cyclohexylidene ester VI, where A and B together represent =CHCOOAlkyl, and $X^1$ and $X^2$ signify hydroxy-protecting groups, is the desired intermediate. These subsequent steps comprise, first, the reduction of the ester (using, for example, LiAlH$_4$ or diisobutylaluminum hydride, DIBAL-H) to the corresponding primary alcohol of structure VII, shown below, where $X^1$ and $X^2$ represent hydroxy-protecting groups, and $Y^1$ is hydroxy. This alcohol, under conventional tosylation or mesylation conditions, may be transformed to the corresponding tosylate or mesylate, structure VII, where $Y^1$ represents —O—SO$_2$PhMe, or —OSO$_2$Me, or, alternatively, the alcohol may be subjected to displacement by halogen, to obtain the corresponding halide, structure VII, where $Y^1$ is a halogen atom, i.e. I, Br or Cl. From the mesylate, tosylate or halide of structure VII, the desired synthon of structure I is now obtained by various generally known conversion reactions. Thus, the halide, tosylate or mesylate, upon treatment with a metal diphenylphosphide and subsequent peroxide oxidation, yields the desired phosphine oxide derivative of structure I, where Y=—P(O)Ph$_2$. Similarly, the halide upon treatment with triethylphosphite under Arbuzov reaction conditions, provides the corresponding phosphonate derivative I, where Y=—P(O)(OEt)$_2$. From the tosylate or mesylate, upon displacement with the sodium salt of an arylsulfinic acid, there can be obtained the aryl-sulfone derivative of compound I, where Y=—SO$_2$Ar. Likewise, upon reaction of the halide VII with trichlorosilane followed by alkylation with an alkylhalide, there is obtained the alkylsilane derivative of compound I, where Y=—Si(Alkyl)$_3$.

The condensation reaction is advantageously conducted by treating the ring A unit of general structure I, dissolved in an organic solvent, with a strong base (e.g. an alkali-metal hydride, alkyl- or aryl lithium, or a lithium alkylamide reagent), so as to generate the anion of I, and then allowing this anion to react with ketone II, so as to achieve condensation to the 19-nor-vitamin analog III, either directly, or via intermediates (e.g. in the case of condensations with compound I where Y=SO$_2$Ar) transformable to III according to known procedures. Any hydroxy-protecting groups (i.e. protecting groups $X^1$ and $X^2$ and/or hydroxy-protecting groups that may be present in the side chain) can then be removed by appropriate hydrolytic or reductive procedures known in the art to obtain the free hydroxy-vitamin analog, structure III, where $X^1$ and $X^2$ represent hydrogen.

Typical Embodiments of the invention and Specific Examples

More specific embodiments of the preparation of the above described ring-A unit are outlined in Schemes I, II, and III, whereas Scheme IV provides a specific embodiment of the condensation reaction to obtain a desired 19-nor-vitamin D compound. In the following description and subsequent examples, Arabic numerals (e.g. 1, 2, 3, etc.), designating specific synthetic products, refer to the structures so numbered in the Schemes.

As shown in Scheme I, the starting material for the preparation of the ring-A unit is the commercially available (1R,3R,4R,5R) (–) quinic acid, designated as compound 1 in Scheme I herein, which already contains the correct stereochemistry of the 1- and 3-hydroxy groups for the desired 19-nor-vitamin D compound. Esterification with methanol in the presence of a catalytic amount of acid (e.g. p-toluene sulfonic acid), followed by treatment with tert-butyldimethylsilyl chloride and triethylamine in dimethyl formamide gave the protected methyl ester 2. It should be noted that esterification with higher alkanols (e.g. ethanol, propanol, etc.) under analogous conditions produces the corresponding higher esters, and that similarly other hydroxy-protecting groups (e.g. other alkyl or arylsilyl groups, or alkoxyalkyl groups) can be introduced at this stage by known methods. Such alternative esters or hydroxy-protected derivatives of 2 can likewise be used in subsequent conversions according to Schemes I, II or III. Reduction of the ester with diisobutylaluminum hydride gave triol 3, and subsequent sodium periodate oxidation produced the cyclohexanone derivative 4. The 4-hydroxy group was protected with an alkylsilyl group to give 5. It is to be noted that because of the symmetry of these ketone intermediates (compounds 4 and 5), the C-4-oxygen substituent can now be depicted as having either the α- or the β-stereochemical orientation. Hence, in accord with convention, the bond to the C-4-oxygen substituent in compounds 4 and 5 is indicated by a wavy line ( $\sim\sim$ ). Three of the subsequent intermediates (compounds 6, 7, and 8) are then obtained as pairs of products, one having the C-4-oxygen substituent in the α-, the other in the β-orientation. This fact is also denoted by a wavy-line bond to the C-4-oxygen substituent in structure 6, 7, and 8 of Scheme I.

A Peterson reaction with ethyl (trimethylsilyl)acetate in the presence of base in anhydrous tetrahydrofuran gave the unsaturated ester 6. Other alkyl (trimethylsilyl)acetate esters (e.g. where alkyl=methyl, propyl, butyl, etc.) can be used in this reaction to give alkyl esters analogous to 6 (e.g. the corresponding methyl, propyl, butyl esters, etc. ). Partial deprotection of the 4-trimethylsilyloxy group with dilute acetic acid in tetrahydrofuran gave 7. The deoxygenation of the 4-hydroxy group was accomplished by a free radical fragmentation procedure [D. H. R. Barton and S. W. McCombie, *J. Chem. Soc. Perkin Trans.*, 1, 1574 (1975); D. H. R. Barton and W. B. Motherwell, *Pure & Appl Chem.*, 53, 15 (1981)]. Thus, ester 7 was converted to the corresponding thioimidazolide 8 by treatment with 1,1-thioicarbonyldiimidezole in an organic solvent, and subsequent radical deoxygenation with tributyltin hydride in the presence of a radical initiator (AIBN) gave the protected cyclohexylidene ester 9. The latter was reduced to the allylic alcohol 10 with diisobutylaluminum hydride which was then converted to the allylic chloride 11 by reaction with the complex made from N-chlorosuccinimide and dimethyl sulfide (E. J. Corey, C. U. Kim, M. Takeda, *Tetrrahedron Letters*, 4339 (1972)] and finally transformed to the desired phosphine oxide 12 on treatment with lithium diphenylphosphide followed by oxidation with hydrogen peroxide.

Scheme II illustrates an alternative method of synthesizing the ring-A unit. In this method, ester 2, obtained as in Scheme I, is directly subjected to the free radical deoxygenation procedure, involving conversion to the thioimidazolide 13, and subsequent treatment with tributyltin hydride to obtain the ester 14. Reduction of compound 14 with diisobutylaluminum hydride (DIBALH) gave diol 15, followed by sodium periodate oxidation to the cyclohexanone derivative 16. Subsequent olefination with ethyl (trimethylsilyl) acetate in the presence of base gave the protected cyclohexylidene ester 9, which is then further processed to the phosphine oxide 12 in the same manner as described in connection with Scheme I.

Scheme III shows yet another modification of the preparation of the ring A-unit. Here the intermediate 4, described previously (see Scheme I), is subjected to free radical deoxygenation procedure using conditions analogous to those described in connection with Scheme I and II. Thus, compound 4 is converted to the thionoimidazol 17 and then reacted with tributyltin hydride in the presence of AIBN to obtain the cyclohexanone derivative 16. Further processing of this material, as in Scheme I and Scheme II, then provides phosphine oxide 12.

In addition to the desired ring-A synthons of general structure I, above, the processes provide other novel intermediates. New compounds are, for example, the intermediates of general structure VII, above, or the cyclohexylidene esters of general structures IV, V and VI, above, where A and B, taken together, represent =CHCOOAlkyl, and of which specific embodiments are illustrated by structures 6, 7, 8, and 9 in Scheme I. Likewise, new are 4-deoxy intermediates of structure VI, above, where A is COOAlkyl, —CH$_2$OH, B is OH, or where A and B, together, represent an oxo group, which examples are provided by structures 14, 15, and 16 in Scheme II. It is also important to note that although these intermediates are generally used in their hydroxy-protected form in the various processes discussed above, the hydroxy-protecting groups ($X^1$, $X^2$, $X^3$) may also be removed, under conditions known in the art, to obtain the corresponding free-hydroxy-intermediates (compounds I, IV, V, VI and VII, where $X^1$ and/or $X^2$ and/or $X^3$ represent H) or be replaced by alternative hydroxy-protecting groups.

In Scheme IV is outlined a specific embodiment of the condensation reaction between phosphine oxide 12 (Scheme I) and a suitable ketone (structure 18) representing rings C and D plus sidechain of the desired 19-nor-vitamin compound. The phosphine oxide 12 was treated with base (butyllithium) at low temperature in tetrahydrofuran to generate the corresponding phosphinoxy anion, which was allowed to react with the hydroxy-protected ketone 18 [Baggiolini et al., *J. Org. Chem.* 51, 3098 (1986)] to give the desired 19-nor-vitamin derivative 19, from which, after protecting-group removal under conventional conditions, there was obtained crystalline 1α,25-dihydroxy-19-norvitamin D$_3$ (20).

EXAMPLE 1

(a) (1R,3R,4R,5R) Methyl 3,5-Bis(tert-butyldimethylsilyloxy)-1,4-Dihydroxycyclohexane-C arboxylate (2)

p-Toluene sulfonic acid (0.5 g) was added to a solution of quinic acid 1 (12.74 g, 66.3 mmol) in methanol. The solution was stirred for 24 h. Solid NaHCO3 (1.0 g) was added and after 15 rain the solution was filtered and concentrated to give 12.61 g (62.16 mmol) of the methyl ester in 92% yield.

tert-Butyldimethylsilyl chloride (6.73 g, 44.62 mmol) was added to a solution of methyl (1R,3R,4R, 5R) (–)quinate (3.68 g, 17.85 mmol) and triethylamine ( 6.2 mL, 44.62 mmol) in 44 mL of anhydrous dimethyl formamide at 0° C. with stirring. After 4 h the solution was warmed to room temperature and stirring continued for another 14 h. The solution was poured into water and extracted with ether. The combined organic layers were extracted with brine, dried over anhydrous $MgSO_4$, filtered and concentrated. The residue was purified by column chromatography on silica gel, eluting with 5–10% ethyl acetate in hexane mixtures, to give 4.6 g (60%) of 2 as a white solid. M.p. 82°–82.5° C. (after recrystallization from hexanes). $^1$H NMR ($CDCl_3$, 500 MHz) δ4.53 (bs, 1H), 4.36 (bs, 1H), 4.11 (ddd, 1H), 3.76 (s, 3H), 3.42 (dd, 1H), 2.31 (bs, 1H), 2.18 bd, 1H), 2.05 (ddd, 2H), 1.82 (dd, 1H), 0.91 (s 9H), 0.89 (s, 9H), 0.15 (s, 3H), 0.14 (s, 3H), 0.11 (s, 3H), 0.09 (s, 3H). MS m/e (relative intensity) 377 (70), 227 (91).

(b) (1R,3R,4R,5R) [3,5-Bis(tert.-butyldimethylsilyloxy)-1,4-dihydroxy]-1-hydroxymethylcyclohexane (3)

Diisobutyl aluminum hydride (45 mL, 45.0 mmol, 1.0M in hexanes) was added to a solution of the ester 2 (3.26 g, 7.5 mmol) in ether (45 mL) at –78° C. After 20 min. the solution was warmed to –23° C. and stirred for 2 h. The solution was diluted with ether and then 2N potassium sodium tartrate was slowly added. The solution was warmed to room temperature and stirred for 15 min. The ether layer was separated and the aqueous layer extracted with ether. The combined ether layers were extracted with brine, dried over anh. $MgSO_4$, filtered and concentrated. The material was further purified by column chromatography on silica gel with 25% ethyl acetate/hexanes to give 83% of 3 (2.52 g, 6.20 mmol), Mp. 108°–109° C. from hexanes. 1H NMR ($CDCl_3$, 500 MHz) δ4.52 (bs, 1H), 4.12 (ddd, 1H) 3.40 (dd, 1H) (dd, 2H), 2.28 (d, 1H) 2.11 (dd, 1H) 2.00 (ddd, 2H), 1.52 (dd, 1H), 1.33 (dd, 1H) 0.91 (s, 9, H) 2.00 (ddd, 2H), 1.52 (dd, 1H), 1.33 (dd, 1H), 0.91 (s, 3H), 0.11 (s, 3H). MS m/e (relative intensity): 349 (8), 331 (13), 239 (12), 199 (100).

(c) (3R,4R,5R) [3,5-Bis(tert.-butyldimethylsilyloxy)-4-hydroxy]-1-cyclohexanone (4)

Sodium periodate saturated water (28.5 mL) was added to the triol 3 (1.91 g, 4.7 mol) in methanol (124 mL) at 0° C. The solution was stirred for 1 h, then poured into water and extracted with ether. The combined ether fractions were washed with brine, dried over anhydrous $MgSO_4$, filtered and concentrated to give 1.72 g (4.59 mmol) of 4 (98%). No further purification was required. Mp. 98°–100° C. from hexanes. $^1$H NMR ($CDCl_3$, 500 MHz) δ4.28 (m, 2H), 3.80 (bs, 1H), 2.77 (dd, 1H, J=14.3, 3.4 Hz), 2.59 (dd, 1H, J=13.1, 10.7 Hz), 2.45 (dd, 1H, J=14.1, 5.2 Hz) 2.25 (bd, 1H, J=15.9 Hz), 0.90 (s, 9H), 0.85 (s, 9H), 0.08 (s, 34H), 0.08 (s, 3H), 0.06, (s, 6H). MS m/e (relative intensity) 317 (62), 231 (16), 185 (76), 143 (100).

(d) (3R,4R,5R) [3,5-Bis(tert.-butyldimethylsilyloxy)-4-trimethylsilyloxy]-1-cyclohexanone (5)

N-(Trimethylsilyl)imidazole (2.52 mL, 26.67 mmol) was added to a solution of the ketoalcohol 4 (1.56 g, 4.167 mmol) in methylene chloride (38 mL). The solution was stirred for 20 h. Water (1 mL) was added and the solution stirred for 30 min. Brine and methylene chloride was added. The brine was extracted with methylene chloride. The combined methylene chloride fractions were dried with anh. $MgSO_4$, filtered and concentrated. The residue was further purified by column chromatography on silica gel with 10% ethyl acetate in hexane to give 5 (1.76 g, 3.95 mmol) in 95% yield. $^1$H NMR ($CDCl_3$, 500 mHz) δ4.25 (m,1H), 4.13 (m, 1, H), 4.04 (m, 1H), 2.74 (ddd, 2H), 2.38 (dd, 1H), 2.19 (dd, 1H), 0.90 (s, 9H), 0.86 (s, 9H), 0.16 (s, 9H), 0.07 (bs, 12 H). MS m/e (relative intensity): 431 (5), 389 (100), 299 (45), 257 (28).

(e) (3R,4R,5R) Ethyl [3,5-bis(tert-butyldimethylsiyloxy)-4-hydroxy]-cyclohexylidene carboxylate (7)

n.Butyl lithium (1.83 mL, 3.106 mmol) 1.5M in hexanes was added to a solution of diisopropylamine (0.43 mL, 3.106 mmol) in anhydrous tetrahydrofuran (2.10 mL) under argon at –78° C. with stirring. After 15 min. the solution was warmed to 0° C. for 15 min. and then cooled to –78° C. and ethyl (trimethylsilyl) acetate (0.57 mL, 3.11 mmol) was added. After 15 min. the protected keto compound 5 (0.6934 g, 1.55 mmol) in anhydrous tetrahydrofuran (2.1+1.0 mL) was added. The solution was stirred for 2 h at –78° C. Water and additional ether were added. The water was extracted with ether and the combined ether fractions were extracted with brine, dried over anhydrous MgSO4, filtered and evaporated. The residue (the protected ester 6) was dissolved in tetrahydrofuran (5 mL), acetic acid (5 mL), and water (1 mL) were added. The solution was stirred for 72 h, then diluted with ether. Saturated sodium bicarbonate was slowly added until no more carbon dioxide evolution was evident. The ether was separated and the bicarbonate solution extracted with ether. The combined ether fractions were extracted with brine, dried over anhydrous $MgSO_4$, filtered and concentrated. The product was further purified by column chromatography, and eluted with ethyl acetate-hexane mixtures (10% to 25% ethylacetate in hexane) to give in 86% yield (two steps) 7. (0.544 g, 1.135 mmol) MS m/e (relative intensity) 429 (4), 399 (6), 387 (100), 341 (46).

(f) (3R,4R,5R) Ethyl [3,5-Bis(tert.-butyldimethylsilyloxy)-4-imidazolyl-thiocarbonyloxy-]cyclohexylidenecarboxylate (8)

1,1-thiocarbonyldiimidazole (0.131 g, 0.735 mmol) was added to a solution of the hydroxy ester 7 (0.163 g, 0.37 mmol) in methylene chloride (1.64 mL). The solution was stirred for 60 h. Silica gel was added and the solution concentrated. The residue was added to a column of silica gel and the material eluted with 25% ethyl acetate in hexane to obtain 8 in 87% yield (0.178 g, 0.32 mmol).

(g) (3R,5R) Ethyl [3,5-Bis-(tert.-butyldimethylsilyloxy)]-cyclohexylidene carboxylate (9)

Tributyltin hydride (0.72 mL, 2.66 mmol) was added to a solution of AIBN (17 mg), and the thionoimidazole it (0.59 g, 1.06 mmol) in degased toluene (106 mL). The solution was heated with stirring to 100° C for 2 h and then concentrated. The residue was further purified by column chromatography on silica gel eluting with hexane, following with 3% and 25% ethyl acetate in hexane to obtain 0.322 g (0.75 mmol) 9 in 71% yield.

$^1$H NMR ($CDCl_3$, 500 MHz) δ5.70 (s, 1H), 4.13 (m, 4H), 3.05 (dd, J=6.74, 6.16 Hz 1H), 2.78 (dd, J=6.96, 2.75 Hz, 1H), 2.38 (dd, J=6.51, 3.25 Hz, 1H) 2.15 (dd, J=7.74, 6.48 Hz, 1H) 1.80 (m, 1H), 1.70 (m, 1H), 1.26 (t, J=7.29 Hz, 3H), 0.87 (s, 9H), 0.85 (s, 9H), 0.04 (s, 12H). MS m/e (relative intensity): 413 (14), 371 (100), 213 (23).

(h) (3R,5R) [3,5-Bis(tert.-butyldimethylsilyloxy)cyclohexylidene] ethanol (10)

A solution of 96mg ester 9 (0.22 mmol) in 2 mL of anhydrous toluene was treated at −78° C. under argon with 0.62 mL (0.92 mmol) of a 1.5M solution of diisobutylaluminum hydride in toluene. After the addition, stirring was continued for 1 h at −78° C. The reaction mixture was then quenched by the addition of 2N potassium sodium tartrate, the organic phase was separated, and the aqueous phase extracted with ethyl acetate. The combined organic phases were washed with water and brine and dried over anhydrous $MgSO_4$, filtered and evaporated. The residue was purified by fast filtration through a silica gel column, using hexane, followed by hexane-ethyl acetate (10:1) as eluent, to give 58 mg (68%) alcohol 10 as a white solid.

$^1$H NMR (500 MHz) δ0.06 (br s, 12H), 0.87 (s, 18H), 1.80 (m, 1H), 2.05 (dd, 1H), 2.18 (br dd J=13, 11 Hz, 1H), 2.34 (m, 1H), 4.02 (m, 2H), 4.13 (m, 2H), 5.60 (br t, J=7.08 1H). MS m/e (relative intensity) 237 (85), 211 (83), 171 (100).

(i) (3R,5R) [3,5-Bis(tert.-butyldimethylsilyloxy)cyclohexylidene]-1-chloroethane (11)

A solution of 50 mg (0.37 mmol) N-chlorosuccinimide in 2 mL of anhydrous dichloromethane was treated at 0° C. under argon with 30 μL (0.41 mmol) dimethyl sulfide. A white precipitate formed. The mixture was stirred an additional 15 min. at 0° C., then cooled to −25° C. and treated with 50 mg (0.13 mmol) of the alcohol 10 dissolved in 0.5 mL of anhydrous dichloromethane. The mixture was stirred under argon for 30 min. at −20° C. and then at 0° C. for 30 min. The reaction mixture was poured on ice, and extracted with ethyl acetate. The organic phase was washed with brine, dried over anhydrous $MgSO_4$ filtered and evaporated. The residue was purified by fast filtration through a silica gel column, eluting with 5% ethyl acetate in hexane to give 52 mg (quant) of the chloro compound 11. $^1$H NMR (CDCl$_3$, 500 MHz), δ0.06 (s, 12H), 0.89 (s, 18H), 1.73 (br dd, 1H), 2.22 (m, 1H) 2.30 (m, 1H), 2.32 (m, 1H), 4.04 (dd, J=7.3, 10.8 Hz, 2H), 4.11 (dd, J=2.87, 10.46 Hz, 2H), 5.51 (brt 1H). MS m/e (relative intensity): 237 (93), 215 (52), 189 (79), 105 (100).

(j) (3R,5R)-[Bis(tert.-butyldimethylsilyloxy)-cyclohexyli-dene]ethyl-diphenylphosphine oxide (12)

40 μL (60 μmol) n.Butyl lithium (1.5M in hexanes) was added to 10 μL (60 μmol) diphenylphosphine in 30 μL anhydrous tetrahydrofuran at 0° C. with stirring under argon. The orange solution was treated at 0° C. with 20 mg (50 μmol) of the allylic chloride 11 in 300+200 μL anhydrous tetrahydrofuran. The resulting yellow solution was stirred an additional 40 min at 0° C. and quenched by the addition of water. Solvents were evaporated under reduced pressure and the residue was dissolved in chloroform. The chloroform layer was shaken twice with 5% hydrogen peroxide. The chloroform layer was separated and washed with aqueous sodium sulfite, water and brine, dried over anhydrous $MgSO_4$, filtered and evaporated. The residue was dissolved in 20% 2-propanol in hexane and passed through a silica SepPak and purified by HPLC (Zorbax-Sil 9.4×25 cm column, 20% 2-propanol in hexane) to give 5.5 mg (22%) of the phosphine oxide 12.

UV (EtOH): λ$_{max}$258,265,272 nm, $^1$H NMR (CDCl$_3$, 500 MHz) δ0.01 (ms, 12H), 0.85 (m s, 18H) 1.65 (m, 2H), 1.91 (m, 1H) 2.00 (m, 1H), 2.22 (br d J=3.2 Hz 1H), 3.05 (dr, J=8.5, 14.9 Hz, 1H), 3.14 (dt, J=8.5, 14.9 Hz, 1H), 3.98 (br s 1H), 5.28 (q, 1H), 7.46 (m, Ar-5H), 7.73 (m, Ar-5H). MS m/e (relative intensity): 570 (M+, 1) 513 (100), 381 (46), 306 (20), 202 (55), 75 (20).

EXAMPLE 2

(a) (1R,3R,4R,5R) Methyl [3,5-Bis(tert.-butyldimethylsilyloxy)1-hydroxy-4-imidaz olylthiocarbonyloxy-cyclohexanone carboxylate (13)

1,1'-Thiocarbonyldiimidazole (0.7 g, 4.0 mmol) was added to a solution of the 1,3-protected methyl quinate 2 (1.1 g, 2.5 mmol) in methylene chloride (10 mL). The solution was stirred at RT for 70 h. The solution was concentrated and purified by column chromatography on silica gel and the product eluted with hexane ethyl acetate mixtures to give 13 (1.2 g, 90%). 1H NMR (CDCl$_3$, 500 MHz) δ0.02 (s, 3H), 0.07 (s, 3H), 0.09 (s, 3H), 0.14 (s, 3H), 0.77 (s, 9H), 0.91 (s, 9H), 2.03 (m, 2H), 2.28 (m, 2H), 3.80 (s, 3H), 4.43 (br, s, 1H), 4.58 (m, 1H), 4.66 (br, s, 1H), 5.52 (dd, 1H, J=2.71, 9.05 Hz), 7.06 (d, 1H, J=1.49 Hz), 7.64 (d, 1H, J=2.76 Hz), 8.38 (s, 1H).

(b) (1R,3R,5R) Methyl [3,5-Bis(tert.-butyldimethylsilyloxy)-1-hydroxycyclohexane carboxylate (14)

Tributyltin hydride (0.72 mL, 2.66 mmol) was added to a solution of AIBN (17 mg), and the thionoimidazole 13 (0.58 g, 1.06 mmol) in degased toluene (106 mL). The solution was heated with stirring to 100° C. for 2 h and then concentrated. The residue was further purified by column chromatography on silica gel eluting with hexane, followed with 3% and 25% ethyl acetate in hexane to obtain 14 (0.322 g, 71%). $^1$H NMR (CDCl$_3$, 500 MHz) δ0.09 (s, 3H), 0.11 (s, 3H), 0.14 (s, 3H), 0.15 (s, 3H), 0.89 (s, 9H), 0.91 (s, 9H), 1.46 (m, 2H), 1.56 (m, 1H), 1.82 (dd, 1H), 2.42 (d, J=12.21 Hz), 2.51 (d, J=13.39 Hz), 3.69 (s, 3H), 4.17 (br, s, 1H), 4.25 (m, 1H).

(c) (1R,3R,5R)-(3,5-Bis(tert.-butyldimethylsilyoxy)-1-hydroxy-1-hydroxymethylcyclohexane (15)

Diisobutyl aluminum hydride (6 mL, 9 mmol, 1.5M in toluene) was added to a solution of the ester 14 (0.56 g, 1.3 mmol) in anhydrous toluene (20 mL) at −78° C. After 20 min the solution was warmed to 0° C. and stirred for 1 h. The solution was slowly quenched by adding to a stirred 0° C. solution of 2N potassium sodium tartrate. Ethyl acetate was added and the organic layer separated and the water phase extracted with ethyl acetate. The combined organic phase was washed with brine, dried over anhydrous $MgSO_4$, filtered and evaporated. The material was further purified by column chromatography on silica gel with ethyl acetate hexane mixtures to give the diol 15 (0.3 g, 59%) $^1$H NMR (CDCl$_3$, 500 MHz) δ0.11 (s, 3H), 0.12 (s, 3H), 0.14 (s, 3H), 0.16 (s, 3H), 0.90 (s, 9H), 0.91 (s, 9H), 1.28 (dd, 1H), 1.43 (dd, 1H), 2.00 (ddd 3H), 2.16 (dd, 1H), 3.33 (dd, 1H), 3.40 (dd, 1H), 4.34 (m, 2×1H).

(d) (3R,5R) [3,5-Bis(tert.-butyldimethylsilyloxy)]-1-cylohexanone (16)

Sodium periodate saturated water (28.5 mL) was added to the diol 15 (1.8 g, 4.7 mmol) in methanol (124 mL) at 0° C. The solution was stirred for 1 h, then poured into water and extracted with ether. The combined ether fractions were washed with brine, dried over anhydrous $MgSO_4$, filtered and concentrated to give 16 (1.5 g, 90%). No further purification was required. $^1H$ NMR ($CDCl_3$, 500 MHz) δ0.11 (s, 3H), 0.12 (s, 3H), 0.14 (s, 3H), 0.15 (s, 3H), 0.91 (s, 9H), 0.90 (s, 9H), 1.94 (m, 2H), 2.35 (m, 2H), 2.54 (m, 2H), 4.35 (m, 2×1H).

(3R,5R) Ethyl [3,5-bis(tert.-butyldimethylsilyloxy)-cyclohexylidene carboxylate (9)

n.-Butyl lithium (1.83 mL, 3.106 mmol) 1.5M in hexanes was added to a solution of diisopropylamine (0.43 mL, 3.106 mmol) in anhydrous tetrahydrofuran (2.10 mL) under argon at −78° C. with stirring. After 15 min the solution was warmed to 0° C. for 15 min and then cooled to −78° C. and ethyl (trimethylsily) acetate (0.57 mL, 3.11 mmol) was added. After 15 min the protected keto compound 16 (0.55 g, 1.55 mmol) in anhydrous tetrahydrofuran (2.1+1.0 mL) was added. The solution was stirred for 2 h at −78° C. Water and additional ether were added. The water was extracted with ether and the combined ether fractions were extracted with brine, dried over anhydrous $MgSO_4$, filtered and evaporated. The product was further purified by column chromatography, and eluted with ethyl acetate-hexane mixtures to give 9 (0.544 g, 86%). $^1H$ NMR ($CDCl_3$, 500 MHz) δ0.04 (s, 12H), 0.85 (s, 9H), 0.87 (s, 9H), 1.26 (t, J=7.29 Hz, 3H), 1.70 (m, 1H), 1.80 (m, 1H), 2.15 (dd, J=7.74, 6.48 Hz, 1H), 2.38 (dd, J=6.51, 3.25 Hz, 1H), 2.78 (dd, J=6.96, 2.75 Hz, 1H), 3.05 (dd, J=6.74, 06.16 Hz, 1H), 4.13 (m, 4H), 5.70 (s, 1H).

EXAMPLE 3

(a) 3,5-Bis(di-butyldimethylsilyoxy)-4-imidazolyl-thiocarbonyl-oxy-1-cyclohexanone (17)

Reaction of hydroxy-ketone 4 with 1,1-thiocarbonyldiimidazole, under conditions analogous to those described in Example 2 (a) provides the thiocarbonylimidazole derivatives of structure 17.

(b) 3,5-Bis(tert.-butyldimethylsilyloxy)-1-cyclohexanone (16)

Treatment of compound 17 as obtained in Example 3(a) with tributyltin hydride in the presence of azaisobutyionitrile in toluene, under conditions analogous to those of example 1(g) provides the cyclohexanone derivative 16.

EXAMPLE 4

1α,25-Dihydroxy-19-nor-vitamin $D_3$ (15)

5.5 mg (10 μmol) phosphine oxide 12 was dissolved in 200 μL anhydrous tetrahydrofuran, cooled to 0° C. and 7 mL (10 μmol) n.butyl lithium (1.5 molar in hexanes) added under argon with stirring. The mixture was cooled to −78° C. and 5 mg (14 μmol) protected ketone 13 added in 200 μL+100 μL anhydrous tetrahydrofuran. The mixture was stirred under argon at −78° C. for 1 h and then at 0° C. for 16 h. 20% Ethyl acetate in hexane was added and the organic phase washed with saturated ammonium chloride solution, 10% $NaHCO_3$ solution, brine, dried over anhydrous $MgSO_4$, filtered and evaporated. The residue was dissolved in 10% ethyl acetate in hexane, passed through a silica SepPak and purified by HPLC in 10% ethyl acetate in hexane (Zorbax Sil 9.4×25 cm column) to give 550 μg of the protected 19-nor vitamin $D_3$ 14. This was dissolved in 500 μL anhydrous tetrahydrofuran and treated with 500 μL of a 1M solution of tetrabutylammonium fluoride in tetrahydrofuran. The mixture was stirred under argon at 50° C. for 50 min. cooled and extracted with ether. The ether phase was washed with 10% $NaHCO_3$ solution, brine and dried over anhydrous $MgSO_4$, filtered and evaporated. The reside was filtered through a silica SepPak and purified by HPLC (Zorbax Sil 9.4×25 cm column, 20% 2-propanol in hexane) to give 100 μg of pure 1α,25-dihydroxy 19-nor-vitamin $D_3$ 15. $^1H$ NMR ($CDCl_3$, 500 MHz) δ0.52 (3H, s, 18-$CH_3$), 0.92 (3H, d, J=6.9 Hz, 21-$CH_3$), 1.21 (6H, s, 26 & 27-$CH_3$), 4.02 (1H, m, 3α-H), 4.06 (1H, m, 1β-H), 5.83 (1H, d, J=11.6 Hz, 7-H), 6.29 (1H, d, J=10.7 Hz, 6-H). UV (in EtOH): $\lambda_{max}$: 243, 251.5, 261 nm, Mass spectrum m/e (relative intensity): 404 (M+, 100), 386 (41) 371 (20), 275 (53), 245 (51), 180 (43), 135 (72), 95 (82), 59 (18). UV (EtOH) $\lambda_{max}$: 243, 251.5, 261 (ε31,300, 34,600, 24,900).

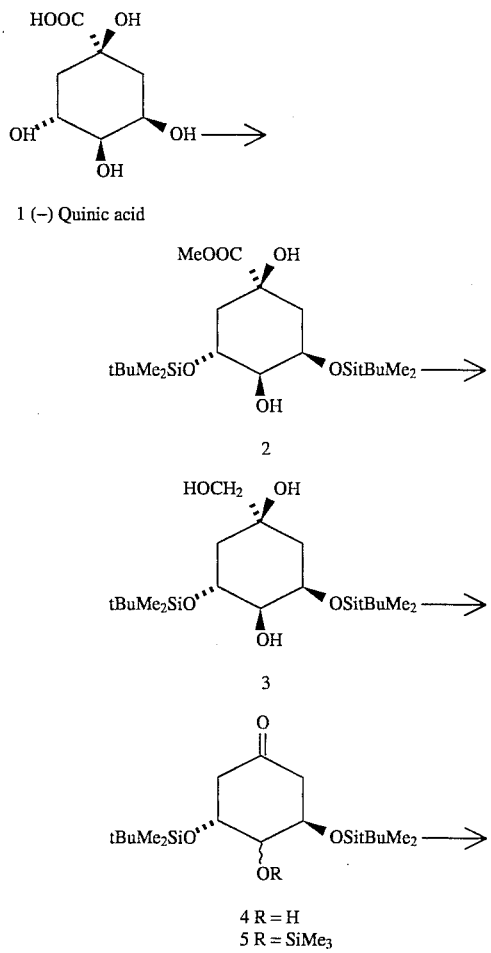

Scheme I.

5,563,286
15
-continued
Scheme I.
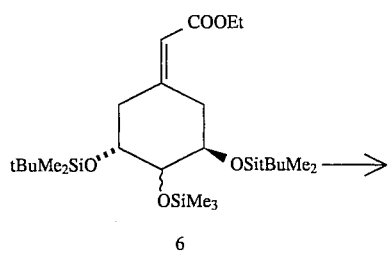
6
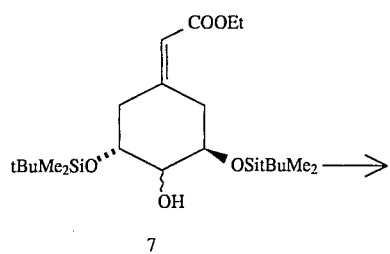
7
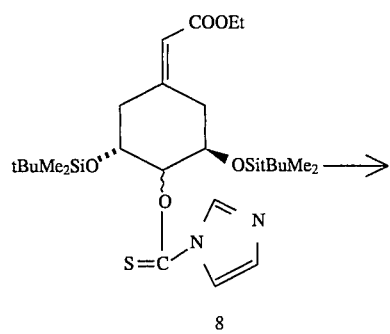
8
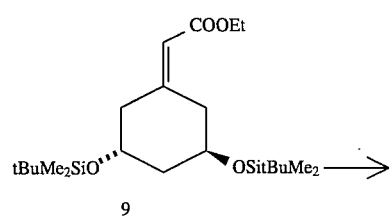
9
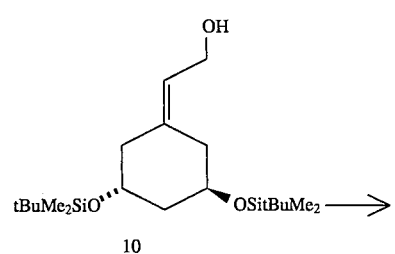
10
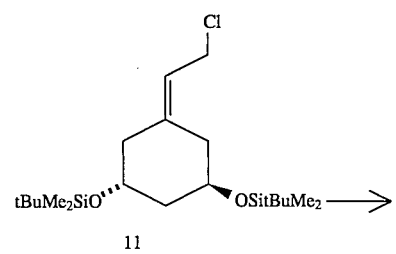
11
16
-continued
Scheme I.
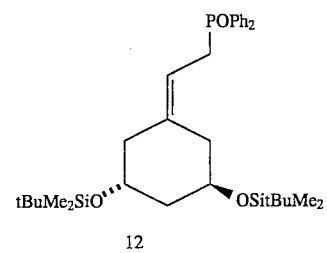
12
Scheme II
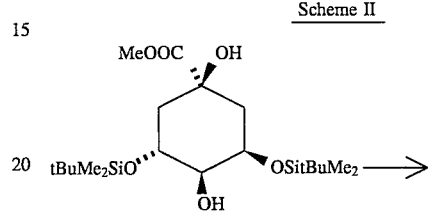
2
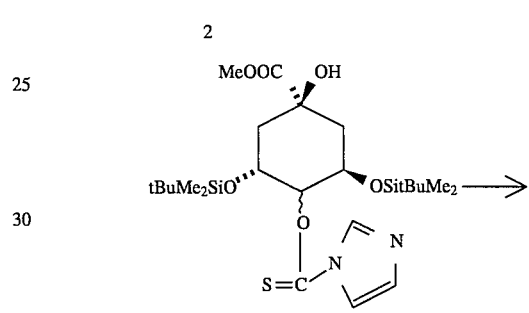
13
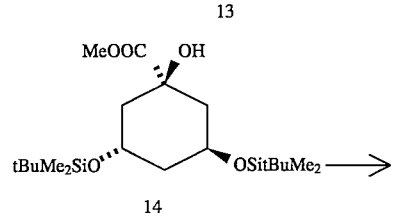
14
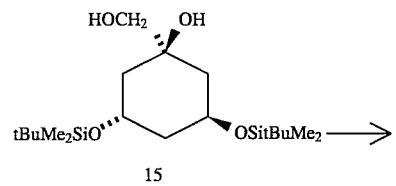
15
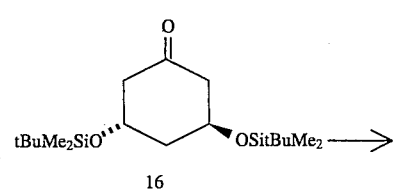
16
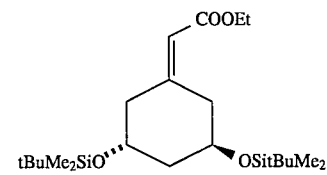
9

Scheme III

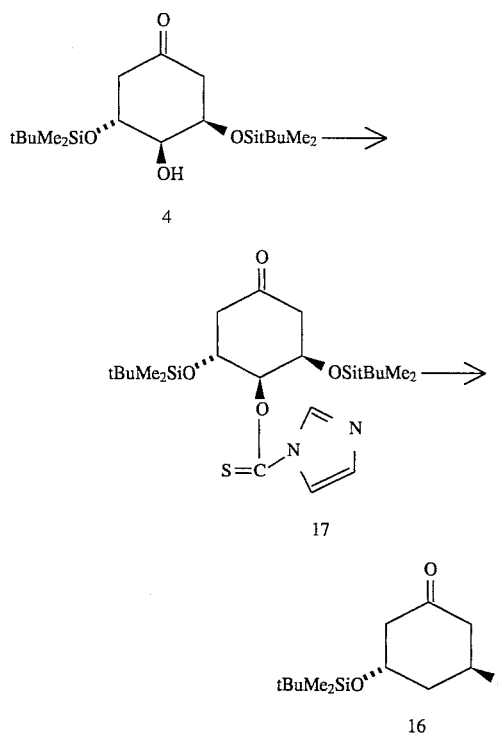

Scheme IV

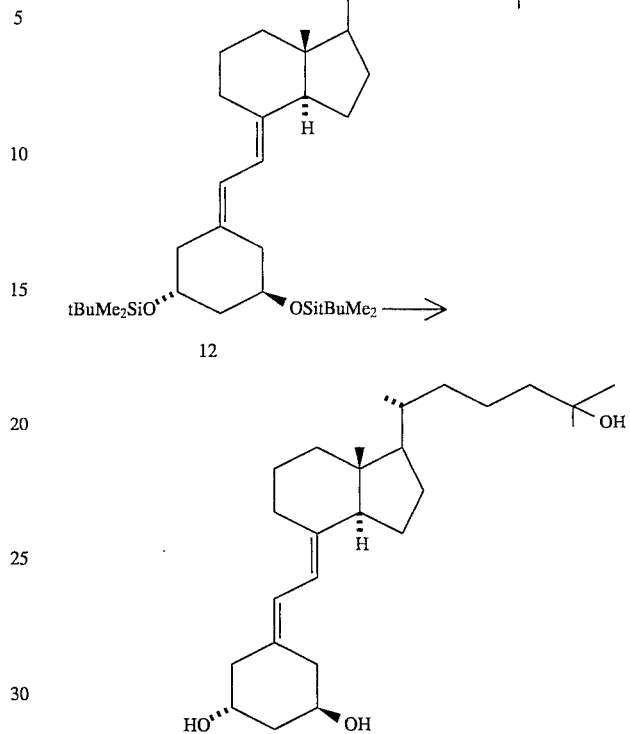

-continued
Scheme IV

We claim:
1. A process for making a compound of the formula

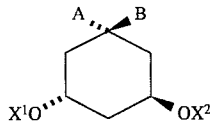

wherein A is —COOAlkyl, and B is hydroxy, or A and B together represent either oxo or =CHCOOAlkyl, and where $X^1$ and $X^2$ are the same or different and represent hydrogen or a hydroxy-protecting group comprising the elimination of the 4-protected hydroxy group in a compound of the formula

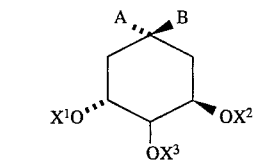

where $X^3$ is

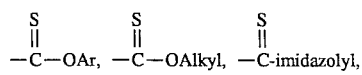

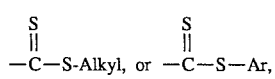

in the presence of a hydrogen radical source and a radical initiator.

* * * * *